(12) United States Patent
Nahon

(10) Patent No.: US 7,322,973 B2
(45) Date of Patent: Jan. 29, 2008

(54) METHOD AND APPARATUS FOR PREVENTING ATRIAL FIBRILLATION

(75) Inventor: Daniel Nahon, Ottawa (CA)

(73) Assignee: CryoCath Technologies Inc., Kirkland, Quebec (CA)

( * ) Notice: Subject to any disclaimer, the term of this patent is extended or adjusted under 35 U.S.C. 154(b) by 598 days.

(21) Appl. No.: 10/815,170

(22) Filed: Mar. 31, 2004

(65) Prior Publication Data

US 2005/0224086 A1  Oct. 13, 2005

(51) Int. Cl.
*A61B 18/02* (2006.01)

(52) U.S. Cl. .......................................... 606/21; 606/20

(58) Field of Classification Search .............. 606/20–26
See application file for complete search history.

(56) References Cited

U.S. PATENT DOCUMENTS

| | | | |
|---|---|---|---|
| 5,487,385 A | 1/1996 | Avitall | |
| 5,575,766 A | 11/1996 | Swartz et al. | |
| 5,673,695 A | 10/1997 | McGee et al. | |
| 5,733,280 A * | 3/1998 | Avitall | 606/23 |
| 5,938,660 A | 8/1999 | Swartz et al. | |
| 6,012,457 A | 1/2000 | Lesh | |
| 6,161,543 A | 12/2000 | Cox et al. | |
| 6,164,283 A | 12/2000 | Lesh | |
| 6,214,002 B1 | 4/2001 | Fleischman et al. | |
| 6,233,491 B1 | 5/2001 | Kordis et al. | |
| 6,241,722 B1 * | 6/2001 | Dobak et al. | 606/23 |
| 6,241,754 B1 | 6/2001 | Swanson et al. | |
| 6,245,064 B1 | 6/2001 | Lesh | |
| 6,292,695 B1 * | 9/2001 | Webster et al. | 607/14 |
| 6,305,378 B1 | 10/2001 | Lesh | |
| 6,325,797 B1 | 12/2001 | Stewart et al. | |
| 6,416,511 B1 | 7/2002 | Lesh et al. | |
| 6,502,576 B1 | 1/2003 | Lesh | |
| 6,511,500 B1 | 1/2003 | Rahme | |
| 6,564,096 B2 | 5/2003 | Mest | |
| 6,652,515 B1 | 11/2003 | Maguire et al. | |
| 6,685,732 B2 | 2/2004 | Kramer | |
| 6,755,822 B2 * | 6/2004 | Reu et al. | 606/21 |

OTHER PUBLICATIONS

Gardner, E., et al., The Nerve Supply and Conducting System of the Human Heart at the End of the Embryonic Period Proper, *J. Anat.* (1976), 121, 3, pp. 571-587.

Gulbenkian, S., et al., Peptidergic Innervation of Human Epicardial Coronary Arteries, *Circulation Research*, vol. 73, No. 3, Sep. 1993, pp. 579-588.

Kalman, J.M., et al., Atrial Fibrillation After Coronary Artery Bypass Grafting is Associated with Sympathetic Activation, *Ann. Thorac. Surg.*, 1995;60:1709-15, pp. 1709-1715.

Aranki, S.F., et al., Predictors of Atrial Fibrillation After Coronary Artery Surgery, *Circulation.* 1996;94:390-397, pp. 390-397.

(Continued)

*Primary Examiner*—Roy D. Gibson
(74) *Attorney, Agent, or Firm*—Christopher & Weisberg, P.A.

(57) ABSTRACT

A method and apparatus for reducing the likelihood of post operative atrial fibrillation by cooling specific nerves in the heart. In an exemplary method, a semi-rigid probe having a distal portion capable of cooling tissue to temperatures below freezing, is placed on tissue proximate cardiac nerves to temporarily or permanently inhibit signal conduction in the nerves.

11 Claims, 7 Drawing Sheets

OTHER PUBLICATIONS

Hogue, C.W. Jr., et al., RR Interval Dynamics Before Atrial fibrillation in Patients after Coronary Artery Bypass Graft Surgery, *Circulation*, 1998;98:429-434, pp. 429-434.

Pasic, M., et al., Surgery for Acquired Cardiovascular Disease, *The Journal of Thoracic and Cardiovascular Surgery*, vol. 118, No. 2, Aug. 1999, pp. 287-296.

Doshi, R.N., et al., Relation Between Ligament of Marshall and Adrenergic Atrial Tachyarrhythmia, *Circulation*. 1999;100-876-883, pp. 876-883.

Jayachandran, J.V., et al., Atrial fibrillation Produced by Prolonged Rapid Atrial Pacing is Associated with Heterogeneous Changes in Atrial Sympathetic Innervation, *Circulation*.2000;101:1185-1191, pp. 1185-1191.

Pauza, D.H., et al., Morphology, Distribution, and Variability of the Epicardiac Neural Ganglionated Subplexuses in the Human Heart, *The Anatomical Record* 259:353-382 (2000), pp. 353-382.

Hogue, C.W., Jr., et al., Atrial fibrillation After Cardiac Operation: Risks, Mechanisms, and Treatment, *Ann. Thorac Surg.* 2000;69:300-6 (2000).

Wu, T-J, et al, Pulmonary Veins and Ligament of Marshall as Sources of Rapid Activations in a Canine Model of Sustained Atrial Fibrillation, *Circulation*, 2001;103;1157-1163.

Creswell, L.L., et al., *Postoperative Atrial Fibrillation: An Old Problem Crying for New Solutions*, The Journal of Thoracic and cardiovascular Surgery, Mar. 2003; vol. 125:S20-3, pp. S20-223.

Bauernschmitt, R., et al., *Depression of a Baroreflex Sensitivity After Cardiac Surgery*, Programme of the $2^{nd}$ EACTS/ESTS Joint Meeting: Abstracts, Abstract No. 195, Oct. 14, 2003, p. 480.

Pappone, C., et al., Pulmonary Vein Denervation Enhances Long-Term Benefit After Circumferential Ablation for Paroxysmal Atrial Fibrillation, *Circulation*. 2004;109-327-334, pp. 327-334.

Melo, J., et al., Ventral Cardiac Denervation Reduces the Incidence of Atrial Fibrillation After Coronary Artery Bypass Grafting, *The Journal of Thoracic and Cardiovascular Surgery*, vol. 127, No. 2, (2004);127-511-6, pp. 511-516.

\* cited by examiner

METHOD AND APPARATUS FOR PREVENTING ATRIAL FIBRILLATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to medical devices and methods, and more particularly to a method and system for preventing post operative atrial fibrillation.

BACKGROUND OF THE INVENTION

Atrial Fibrillation (AF) is a common disorder related to abnormal beating of the heart. Specifically, instead of beating in a normal rhythm, the heart's two small upper chambers (the atria) quiver such that blood is not completely pumped from the atria. The residual blood may form a clot with devastating consequences. For example, if a piece of a blood clot formed in the atria leaves the heart and becomes lodged in an artery in the brain, a stroke may result. In fact, about 15 percent of strokes are related to atrial fibrillation.

It is well documented that atrial fibrillation (AF), either alone or as a consequence of other cardiac disease, continues to persist as the most common type of cardiac arrhythmia. In the United States alone, AF currently affects an estimated two million people, with approximately 160,000 new cases being diagnosed each year. The cost of treatment for AF is estimated to be in excess of $400 million worldwide each year.

Post operative AF is a significant problem for hospitals worldwide with no effective solution. AF is the most common morbidity event after coronary bypass grafting. It has been estimated that the incidence of AF following coronary artery bypass graft (CABG) surgery is between 25% and 40%. The rate is even higher for patients undergoing valve surgery either alone or in combination with CABG surgery. Although the AF may resolve itself within the first ten days following surgery, the problem is associated with high levels of morbidity during the post operative phase and can increase the cost of hospital stays by $20,000 or more.

Although pharmacological treatment is available for AF, the treatment is far from perfect. For example, certain antiarrhythmic drugs, like quinidine and procainamide, can reduce both the incidence and the duration of AF episodes. Yet, these drugs often fail to maintain sinus rhythm in the patient. Cardioactive drugs, like digitalis, Beta blockers, and calcium channel blockers, can also be given to control AF by restoring the heart's natural rhythm and limiting the natural clotting mechanism of the blood. However, antiarrhythmic drug therapy often becomes less effective over time. In addition, while drug therapy may mitigate the incidence of AF once it develops, it does nothing to prevent the problem from occurring.

Some investigators have attributed the cause of post-operative AF to an imbalance within the autonomic nervous system of the heart. The autonomic nervous system includes parasympathetic and sympathetic nerves. The parasympathetic pathway acts through a branch of the vagus nerve, which enters the heart near the ascending aorta. The sympathetic pathway acts through a nerve bundle called the cardiac plexus, which enters the heart within the Ligament of Marshall (LOM) as well as at other locations proximal to the cardiac plexus. The LOM is a fold of the pericardium from a developmental vestige of the left primitive veins, near the left atrial appendage. Under normal conditions, there is a balance between the sympathetic and parasympathetic stimulation of the heart. However, following surgery, there is an imbalance in the autonomic system resulting in an over-stimulation of the sympathetic pathway and/or an under-stimulation of the para-sympathetic pathway. This imbalance, due to the temporarily depressed parasympathetic activation following surgery, possibly due to surgical trauma, edema and general side effects of cardiac surgery, could likely result in post operative atrial fibrillation.

Attempts have been made during surgery to prevent post-operative AF. For example, surgical denervation methods remove the nerve supply to tissue by cutting or crushing the axons of nerve cells. On exemplary process, ventral cardiac denervation, entails the removal of nerves around large vessels at the base of the heart that run from the right side of the superior vena cava and end at the level of the midportion of the anterior pulmonary artery. The dissection starts at the right side of the pericardial cavity and the superior vena cava is completely dissected and separated from the right pulmonary artery. Then the fat pad around the aorta is dissected. Finally, all of the fatty tissues in the aorta-pulmonary groove and the inner half of the adventitia of the anterior pulmonary artery up to the left border are cut.

Another technique intended to prevent non post-operative AF is radiofrequency catheter ablation, wherein a catheter having an electrode at its tip is guided to an area of heart muscle having an accessory pathway. The catheter is placed at the exact site inside the heart where cells give off electrical signals that stimulate the abnormal heart rhythm. Radiofrequency energy transmitted through the pathway kills heart muscle cells in the specific area. Therefore, that area can no longer conduct the extra impulses that caused the rapid heartbeats.

Although radiofrequency ablation may be effective in some patients when medications don't work, the burst of radiofrequency energy destroys the tissue that triggers the abnormal electrical signals. Further, radiofrequency ablation techniques may lead to injury of contiguous structures, the development of thrombus and the risk of pulmonary vein stenosis. Finally, atrial pacemakers have been used as a treatment of AF. Pacemakers are implanted under the skin to regulate the heart rhythm of the patient. This, and the aforementioned procedures are invasive and non-reversible and place patients exhibiting symptoms of post operative atrial fibrillation at unnecessary risk.

In view of the above treatment limitations, it would be desirable to provide a reversible method and system of treating the nerves of the heart in order to reduce or eliminate sympathetic nerve stimulation to the heart in order to reduce the likelihood of postoperative atrial fibrillation.

Also in view of the above, it would also be desirable to provide a permanent method and system of treating the nerves of the heart without causing significant damage to adjacent structures thereby limiting the risk of pulmonary vein stenosis, thrombus formation or endocardial disruption.

SUMMARY OF THE INVENTION

The present invention provides a reversible method of reducing the likelihood of atrial fibrillation after heart surgery. The method includes the step of reducing the temperature of selective nerve tissue with a cooling device until the nerve tissue is temporarily disabled. The cooling device can include a flexible catheter, a semi-rigid probe, or a rigid probe capable of chilling and freezing nerve tissue.

In an exemplary procedure, the target tissue region is the posterior surface of the left atrium of the heart near a vestigial fold of the pericardium known as the Ligament of Marshall (LOM). By treating specific nerve regions in the heart for a predetermined period of time, until the nerve tissue reaches a predetermined temperature, the stimulation of the sympathetic nerve division of the autonomic nervous system can be controlled.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention uses a device to cool and/or freeze bundles of nerve tissue at strategic locations on a patient's heart during surgery in order to prevent the occurrence of post-operative atrial fibrillation. One type of cooling device that is compatible for use with the present invention is disclosed in U.S. Pat. No. 6,669,689, the disclosure of which is incorporated herein by reference. Preferably, the device is placed on the posterior surface of the left atrium proximate the Ligament of Marshall (LOM) or near on the superior portions of the left and right atriums where are located the richly enervated fat pads at these locations. This is done to ablate the sympathetic nerves within the LOM. It is the over-stimulation of the sympathetic pathway which often leads to atrial fibrillation. In an alternate embodiment, the device is placed directly on the LOM and the LOM is cooled by the device in order to temporarily disable the nerves around the LOM and act as an anesthetic. Unlike other denervation procedures that incorporate invasive and non-reversible incisions, the cooling and/or freezing of specific locations in the heart has a reversible effect on the nerves. Alternatively a similar approach can be used near the atrial fat pads.

Figure 1:
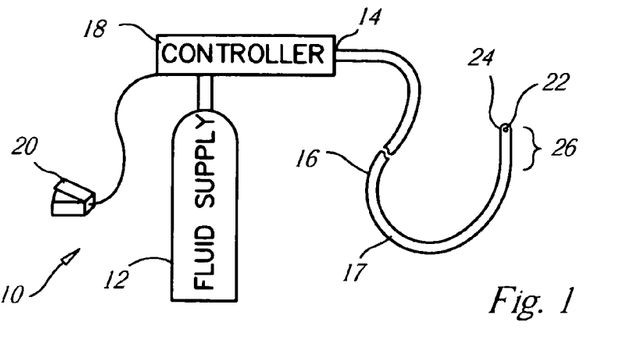
FIG. 1 is a schematic illustration of an embodiment of a cryosurgical system used with the present invention.

FIG. 1 is a schematic illustration of a cryosurgical system 10 used accordance with the invention. The system 10 includes a supply of cryogenic or cooling fluid 12 in communication with the proximal end 14 of a cryogenic catheter 16. Although a catheter is shown in the cryosurgical system of FIG. 1, the present invention will operate with other ablation devices. In the foregoing discussion, reference will be made to an ablation or cooling device but all points and discussion will apply as well to flexible, semi-rigid, or rigid catheters and probes type devices, as well as devices using combinations and portions thereof.

Referring once again to FIG. 1, fluid controller 18 is interposed or in-line between the cryogenic fluid supply 12 and the catheter 16 for regulating the flow of cryogenic fluid into the catheter in response to a controller command. Controller commands can include programmed instructions, sensor signals, and manual user input. For example, the fluid controller 18 can be programmed or configured to increase and decrease the pressure of the fluid by predetermined pressure increments over predetermined time intervals. In another exemplary embodiment, the fluid controller 18 can be responsive to input from a manual control, such as a foot pedal 20, to permit flow of the cryogenic fluid into the catheter 16.

One or more flow controllers or temperature sensors 22 in electrical communication with the controller 18 can be provided to regulate or terminate the flow of cryogenic fluid into the catheter 16 when a predetermined temperature at a selected point or points on or within the catheter is/are obtained. For example, a temperature sensor can be placed at a point proximate the distal end 24 of the catheter and other temperature sensors 22 can be placed at spaced intervals between the distal end of the catheter 16 and another point that is between the distal end 24 and the proximal end 14.

The cryogenic fluid used can be in a liquid state, a gas state, or mixed phase. An extremely low temperature can be achieved within the catheter, and more particularly on the surface of the catheter by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include nitrous oxide, argon, and carbon dioxide.

Catheter 16 includes a flexible member 17 having thermally-transmissive region 26 and a fluid path through the flexible member 17 to the thermally-transmissive region 26. A fluid path is also provided from the thermally-transmissive region 26 to a point external to the catheter, such as the proximal end 14. Exemplary fluid paths can be one or more channels defined by the flexible member 17, and/or by one or more additional flexible members that are internal to the first flexible member 17. Also, even though many materials and structures can be thermally conductive or thermally transmissive if chilled to a very low temperature and/or cold soaked, as used herein, a "thermally-transmissive region" is intended to broadly encompass any structure or region of the catheter 16 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an target nerve tissue can be performed in a single or multiple cycle process without having to relocate the catheter one or more times or drag it across tissue.

In exemplary embodiments of the invention, the thermally-transmissive region 26 of catheter 16 may be deformable. An exemplary deformation is from a linear configuration to an arcuate configuration and is accomplished using mechanical and/or electrical devices known to those skilled in the art. For example, a wall portion of the flexible member 17 can include a metal braid to make the catheter torqueable for overall catheter steering and placement. Additionally, a cord, wire or cable can be incorporated with, or inserted into, the catheter for deformation of the thermally transmissive region 26.

Having described the function of the cryogenic catheter 16 and its use in a system context, several exemplary embodiments of the thermally-transmissive region 26 of the catheter 16 are now described in greater detail. FIGS. 2-6 illustrate embodiments of the catheter, or portions thereof, having two or more thermally-transmissive segments in a spaced-apart relationship. Each of the illustrated catheters includes a closed tip 28 that can include a thermally-transmissive material.

Figure 2:
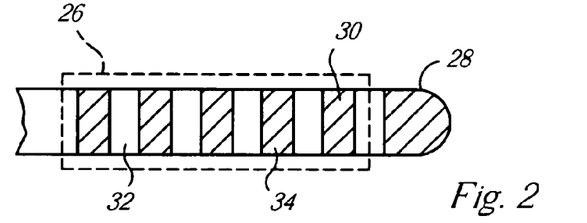
FIG. 2 illustrates the tip region of one embodiment of a catheter that maybe used with the present invention.

Referring specifically to the embodiment depicted in FIG. 2, multiple thermally-transmissive elements 30 are integral with a distal portion of a catheter. Each of the thermally-transmissive elements 30 includes a first side or face (not shown) exposed to a cryogenic fluid path and cryogenic fluid and a second side or face (not shown) exposed to points exterior to the catheter. The first side and/or second side of any or all of the thermally-transmissive elements 30 can be substantially flush with, recessed below, or protruding from the inner surface and outer surface of a portion of the catheter. The thermally-transmissive elements 30 are separated by flexible portions of material 32 than can range from slightly less thermally-transmissive than the adjacent thermally-transmissive elements to substantially less thermally-transmissive than the adjacent elements.

In the illustrated embodiment of FIG. 2, the thermally-transmissive elements 30 are annular, cylindrical elements which are made of gold-plated copper or bronze. Thermocouples 34 can be associated with one or more of the elements 30 and the tip 28. The thermally-transmissive elements 30 can be completely exposed, embedded, or a combination thereof along the full 360 degrees of the catheter's circumference. In certain applications the thermally-transmissive elements traverse or define less than 360 degrees of the catheter's circumference. The longitudinal width of each thermally-transmissive element 30, the spacing between elements, the material thickness, and the material composition are matched with a selected cryogenic fluid, one or more cryogenic fluid delivery locations within the catheter and fluid delivery pressure to produce overlapping cold regions which produce a linear lesion.

Figure 3:
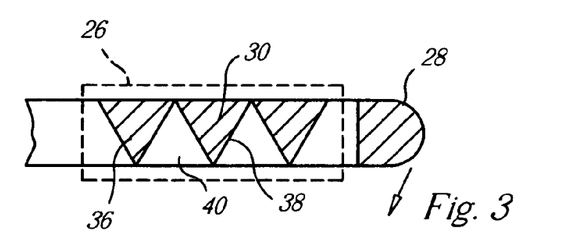
FIG. 3 illustrates an alternative embodiment of the catheter of FIG. 2.

The embodiment illustrated in FIG. 3 is substantially identical to the embodiment of FIG. 2, however, at least one of the thermally-transmissive elements 30 includes a first open end 36 that defines a first plane and a second open end 38 that defines a second plane, wherein the first and second planes intersect to give the annular elements a wedge-like appearance. Such a configuration permits adjacent thermally-transmissive elements 30 to be positioned very closely together, but it can limit the possibilities for deforming the thermally-transmissive region 26, which, in this embodiment, is flexible in the direction indicated by the arrow.

Figure 4:
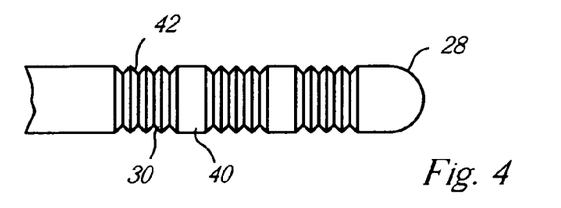
FIG. 4 illustrates yet another embodiment of the catheter used with the invention.
Figure 5:
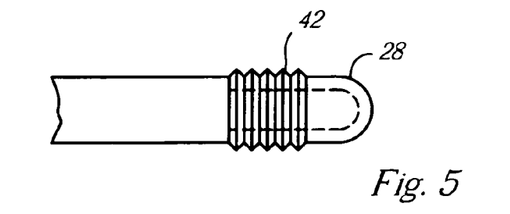
FIG. 5 illustrates a deformable tip for a catheter.

With respect to the embodiments shown in both FIGS. 4 and 5, the thermally-transmissive elements 30 are substantially rigid and are separated and/or joined by a flexible material 40. However, in other embodiments the thermally-transmissive elements 30 are flexible and are interdigitated with either rigid or flexible segments. FIG. 4, for example, illustrates an embodiment of the cryogenic catheter having three thermally-transmissive elements 30 that are flexible. The flexibility is provided by a folded or bellows-like structure 42. In addition to being shapeable, a metal bellows can have enough stiffness to retain a selected shape after a deforming or bending step.

Instead of, or in addition to, flexible, thermally-transmissive elements 30 and/or flexible material 40 between elements, the distal tip 28 (or a portion thereof) can be deformable. For example, FIG. 5 illustrates a tip 28 having thermally-transmissive, flexible, bellows 42.

Figures 6, 7:
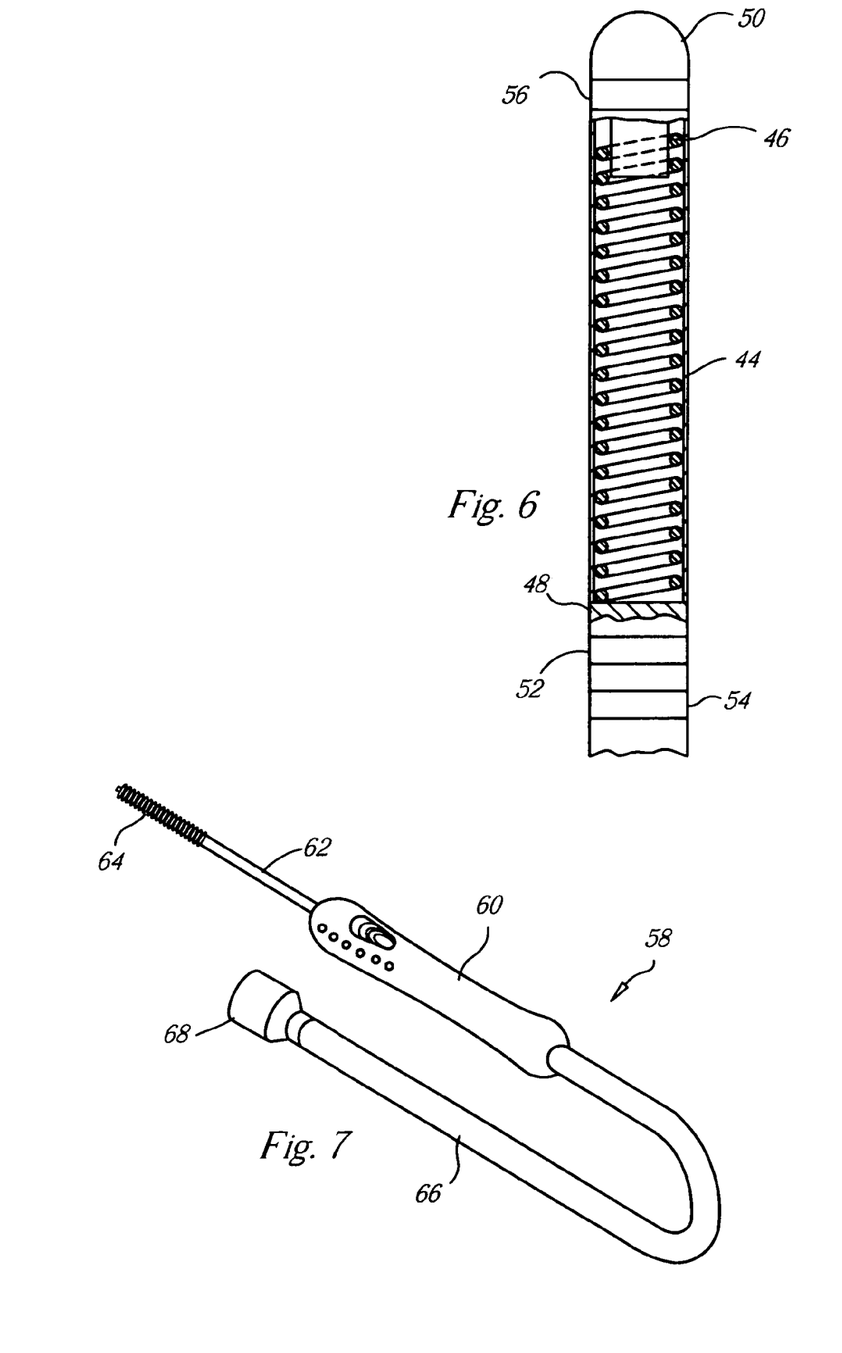
FIG. 6 depicts still another catheter embodiment.
FIG. 7 is a perspective view of an exemplary malleable cryogenic probe that may be used with the present invention.

FIG. 6 illustrates still another embodiment of a cryogenic cooling structure that includes a surface or wall 44 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 44 allows it to readily collapse or otherwise deform under vacuum or near vacuum conditions applied to evacuate fluid/gas from the structure. Accordingly, the structure is provided with one or more supporting elements 46 such as a spring. The cooling structure is illustrated in association with a catheter 48 having a closed distal tip 50 and mono or bipolar ECG rings 52, 54, 56. The thermally-transmissive region is approximately 30 mm in length and is effective for thermal transfer over its entire circumference. However, the thermally-transmissive region may be confined to specific region(s) of the device's circumference.

An illustration of another type of ablation device that may be used in accordance with the present invention is a cryogenic probe of the type shown in FIG. 7. The probe includes a relatively thin and malleable tube suitable for epicardial procedures. At least a portion of the tube has a high thermal conductivity. An even smaller and coolant supply tube is contained within the outer exhaust tube and terminates at a small nozzle within, and adjacent the end of, the distal tip thereof.

A gas, such as argon or nitrous oxide, from a high pressure source is then passed through the inner tube and expands from the nozzle at its end. This cools the tip by the well known Joule-Thompson effect. When sufficient cooling or freezing has taken place, the input can switch to a low pressure gas supply. The low pressure, substantially room temperature, gas simply floods the entire tube and tip to warm, and thereby defrost, the tip to reverse any cryoadhesion and permit the probe to be withdrawn.

As shown in FIG. 7, one embodiment of a cryogenic probe 58 includes a handle 60 with a shaft 62 extending therefrom, where the shaft 62 includes a thermally-transmissive region 64 distal to the handle 60. Flexible member 66 and connector 68 are affixed to the handle 60 for connecting the probe 58 to a control unit 18 (shown in FIG. 1). The handle 60 facilitates handling and manipulation of the shaft 62 and thermally-transmissive region 64, and can include controls for regulating the shape and function of the shaft 62 and the thermally-transmissive region 64.

The shaft 62 can be semi-rigid, having rigidity such that the shaft 62 retains one shape until being influenced to a further shape by the application of moderate pressure on the shaft 62. The malleability stiffness of the shaft 62 can vary depending upon the desired application. The stiffness of the shaft 62 is generally such that a surgeon can bend the shaft 62 by hand to a desired contour with the application of moderate pressure. However, it is understood that its stiffness may, as a whole or in particular regions, may be such that additional tools, e.g., pliers, are required or desirable for exerting enough force to change the shape of the shaft 62. In an exemplary embodiment, shaft 62 can have a length from about 15 cm to 60 cm. The thermally-transmissive region 64 can be flexible, passively or selectively deformable and can assume a linear, curved, circular or irregular shape as required to conform to a tissue surface to be treated. The shape of the thermally-transmissive region 16 can be controlled using pull wires and shims.

Alternatively, the thermally-transmissive region 64 can be semi-rigid, having rigidity such that the thermally-transmissive region 64 retains one shape until being influenced to a further shape by the application of moderate pressure on the thermally-transmissive region 64. The malleability stiffness of the thermally-transmissive region 64 can vary depending upon the desired application. The stiffness of the thermally-transmissive region 64 is generally such that a surgeon can bend the thermally-transmissive region 64 by hand to a desired contour with the application of moderate pressure. However, it is understood that its stiffness may, as a whole or in particular regions, may be such that additional tools, e.g., pliers, are required or desirable for exerting enough force to change the shape of the thermally-transmissive region 64.

Figures 8, 9, 13:
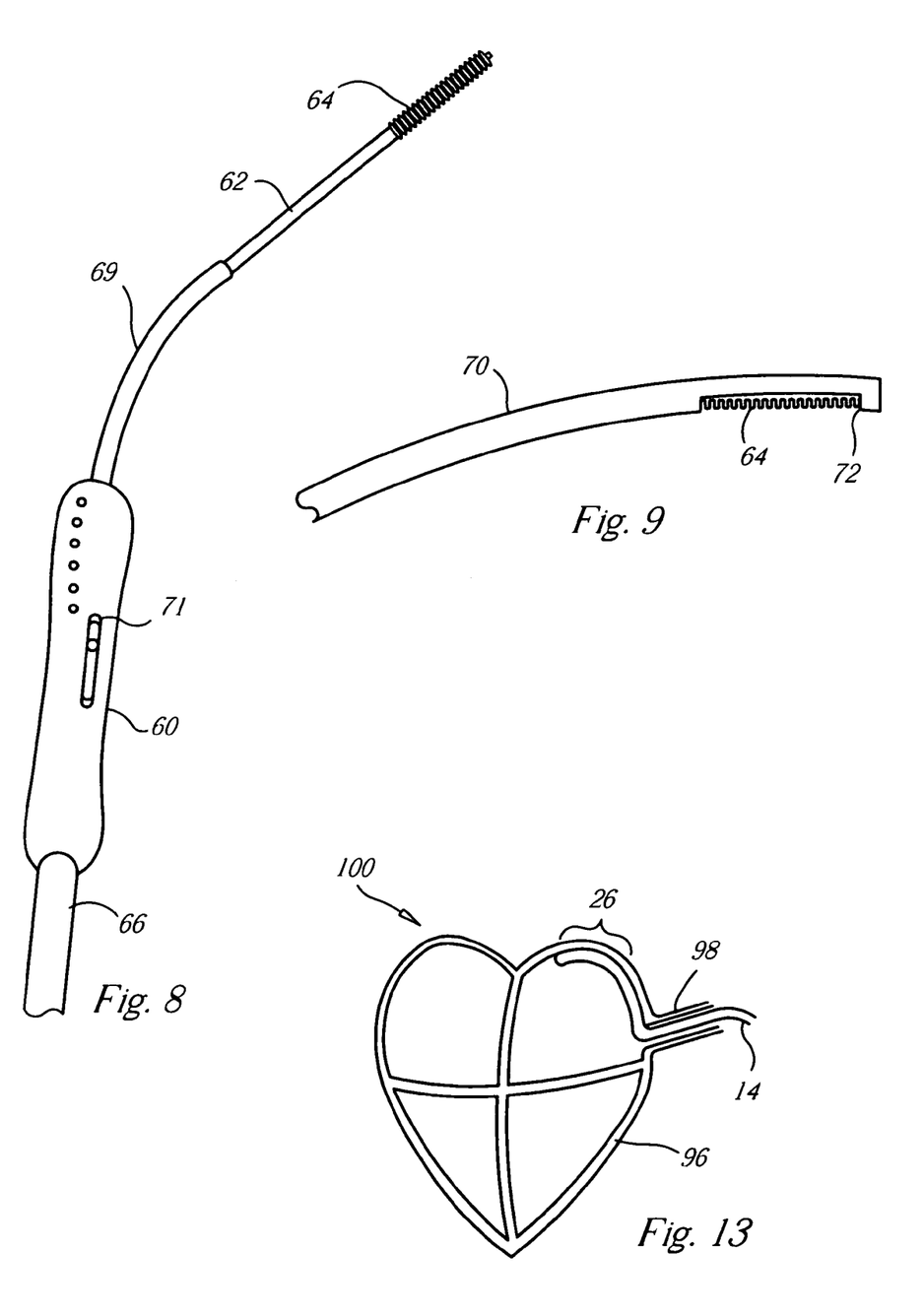
FIG. 8 is a perspective view of the exemplary cryosurgical probe of FIG. 7 including an adjustable insulation sleeve.
FIG. 9 is a perspective view of the insulation sleeve of FIG. 8.
FIG. 13 is a schematic depiction of the chambers of the heart showing placement of the catheter of FIG. 2.

As shown in FIG. 8, an adjustable insulation sleeve 69 can be placed about the shaft 62 and the thermally-transmissive region 64, where the adjustable insulation sleeve 69 is actuated with a slidable lever 71 on the handle 60. The adjustable insulation sleeve 69 can be used to increase or decrease the exposed portion of the thermally-transmissive region 64, allowing for selective tissue treatment. Additionally, the adjustable insulation sleeve 69 protects adjacent tissue from being damaged. For example, where the thermally-transmissive region 64 has a longitudinal length of about 100 mm, the adjustable insulation sleeve 69 can be used to vary the exposed portion of the thermally-transmissive region 64 from about 10 mm to about 100 mm.

In an alternative embodiment, as shown in FIG. 9, a flexible insulation sleeve 70 can be placed about the shaft 62 and the thermally-transmissive region 64, where the insulation sleeve 70 includes a slotted segment 72,which only partially circumferences the thermally-transmissive region 64. The slotted segment 72 forms a partial circumferential blanket or insulating pad, which prevents thermal action from affecting tissue on one side of the thermally-transmissive region 64, while leaving the other side exposed for contact with tissue.

Alternatively, the insulation sleeve 70 can have rigidity such that the insulation sleeve 70 retains one shape until being influenced to a further shape by the application of moderate pressure on the insulation sleeve 70. The malleability stiffness of the insulation sleeve 70 can vary depending upon the desired application. The stiffness of the insulation sleeve 70 is generally such that a surgeon can bend the insulation sleeve 70 by hand to a desired contour with the application of moderate pressure. However, it is understood that its stiffness may, as a whole or in particular regions, may be such that additional tools, e.g., pliers, are required or desirable for exerting enough force to change the shape of the insulation sleeve 70. Additional details regarding the malleable shaft and insulation feature are disclosed in U.S. Pat. No. 6,270,476 which is incorporated herein by reference.

The handle 60, shaft 62, and thermally-transmissive region 64 are substantially hollow and define a lumen to accommodate one or more conduits, wires and/or tubes that can ultimately extend to the distal end of the probe. Generally, the conduits and/or wires extend proximally from the handle 60 through the tubing 66 for connection to the control unit 18 as described above with respect to FIG. 1. In one embodiment, an electrical conduit, a vacuum conduit and a refrigerant conduit extend within the lumen. The electrical conduit provides a passageway for electrical leads to one or more devices, such as at least one thermocouple disposed within the distal portion of the probe for providing temperature information.

Figure 10:
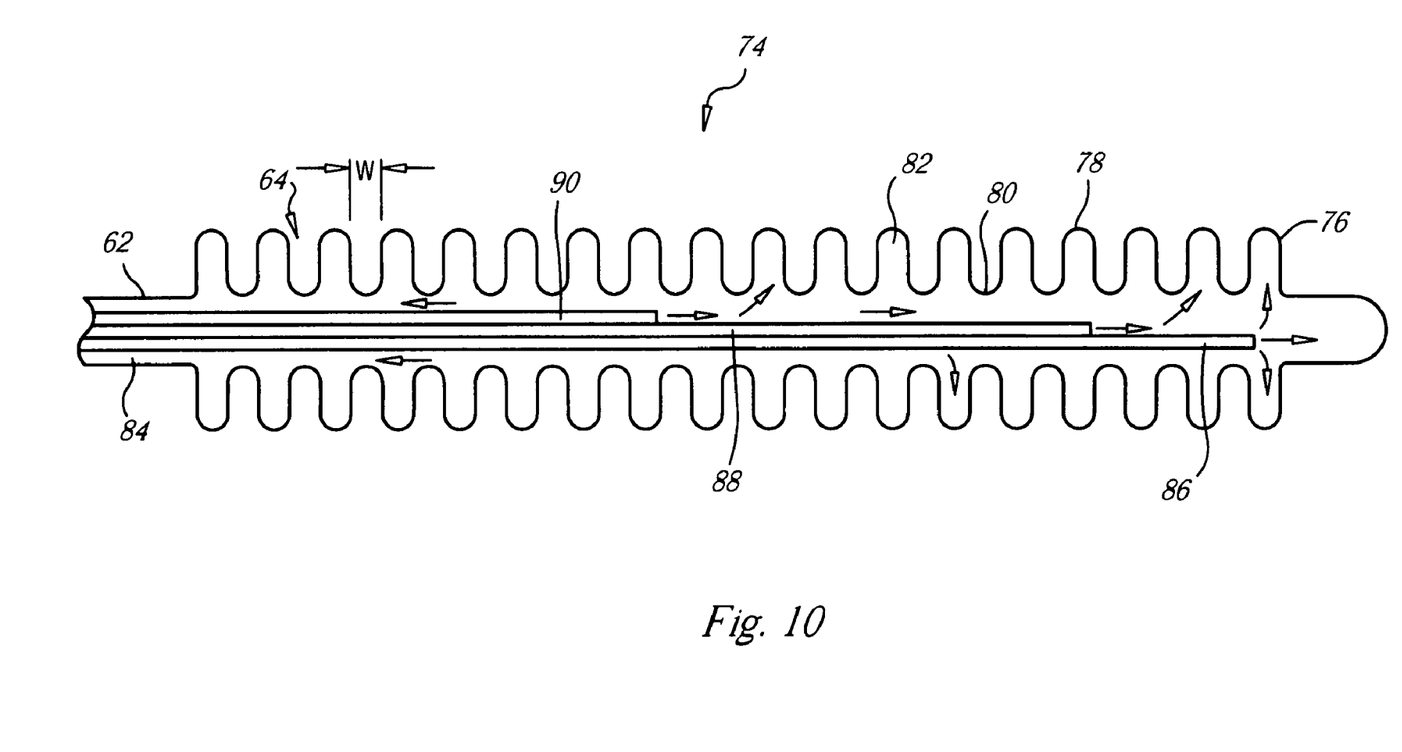
FIG. 10 is an expanded view of the bellows tip configuration of FIG. 7.

FIG. 10 is an expanded view of a bellows configuration 74, wherein the bellows configuration 74 includes a plurality of hollow annular portions 76 joined together at their inner ends 78 and spaced apart at their outer radial ends 80. The hollow annular portions 76 are joined in such a manner to allow the hollow annular portions 76 to bend or deflect with respect to adjacent hollow annular portions 76.

The multiple hollow annular portions 76 are integrated about the circumference of and longitudinally traverse the thermally-transmissive region 64 such that the interior 82 of each hollow annular portion 76 is exposed to the fluid pathway and fluid (shown by arrows). The hollow annular portions 76 and thermally-transmissive region 64 are substantially hollow and define an outer lumen 84 to accommodate one or more inner lumens, wires and/or tubes that can ultimately extend to the distal end of thermally-transmissive region 64. For example, the controller 18, as shown in FIG. 1, allows or causes cryogenic fluid to flow from the cryogenic fluid supply 12 to the fluid path in the catheter 16 and thence through the thermally-transmissive region 64 and the hollow annular portions 76 to thermally treat the desired area.

The longitudinal length of the thermally-transmissive region 64 and the radial height and spacing of the hollow annular portions 76 are configured such that the thermally-transmissive region 64 can be deflected about a radius without impeding the fluid pathways through the thermally-transmissive region 64. The hollow annular portions 76 also result in an increase in the surface area of the thermally-transmissive region 64. The longitudinal length "L" of the thermally-transmissive region 64 can be about 10 mm to 100 mm, and have a diameter "d" of about 1 mm to 6 mm. The hollow annular portions 76 are spaced apart along the thermally-transmissive region's longitudinal length at a distance "w," such that the thermally-transmissive region 64 can be deflected about an arc without the thermally-transmissive region 64 or the hollow annular portions 76 kinking.

In an exemplary embodiment, the outer radial ends 78 and the inner ends 78 have about a 0.5 mm radius 76 the depth of the spaces between the hollow annular portions 76 is about 2 mm. The hollow annular portions 76 have limited axial compression and have a kink radius of less than 15 mm.

The thermally-transmissive region 64 is illustrated having three flexible members or injection tubes 86, 88, and 90 disposed within the outer lumen 84. The inner flexible members 86, 88, and 90 are arranged in a staggered configuration within the outer lumen 84. As used herein, the term "staggered" may be used to designate both a linearly/axially staggered configuration and alternatively, a rotationally staggered configuration. The flexible members 86, 88, and 90 thus define multiple staggered fluid paths within the outer lumen 84. In such a configuration, the injection tubes 86, 88, and 90 allow for greater aggregate cooling power as well as the creation of a variety of different cooling/freeze zones along the length of the outer lumen 84. Additionally, alternative configurations may be utilized for defining a fluid path into and out of the thermally-transmissive region 64.

Figure 11:
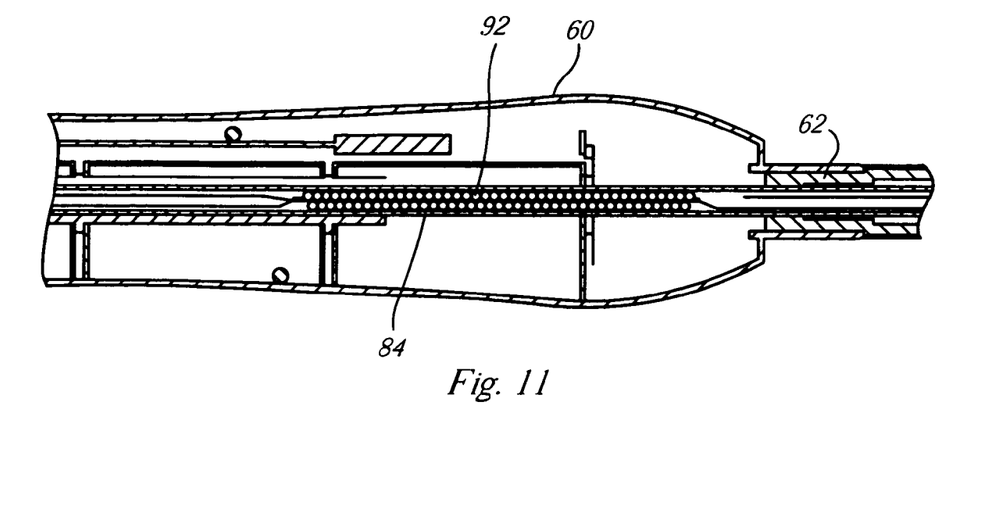
FIG. 11 is a sectional view of the handle of the exemplary cryosurgical probe of FIG. 7.

Referring to FIG. 11, the handle 60 can include a heat exchanger where a helically coiled fluid supply line 92 is disposed within the outer lumen 84. The helically coiled fluid supply line 92 is connected to the injection tubes 86, 88, and 90, supplying fluid to the thermally transmissive region 64. The expanded gas is exhausted through the outer lumen 84 over the helical gas supply line, pre-cooling and condensing the incoming fluid allowing the thermally transmissive region 64 to obtain lower temperatures. The helically coiled fluid supply line 92 is made of metal or another material that readily conducts heat. For example, the helically coiled fluid supply line 92 can be made from nickel, copper, silver, gold, aluminum, stainless steel, or other suitable conductive material.

Figure 12:
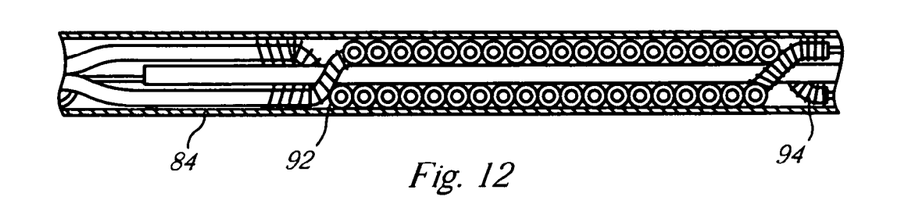
FIG. 12 is a sectional view of the helically coiled fluid supply line of FIG. 11 including finned tubing.

In one embodiment, as shown in FIG. 12, the helically coiled fluid supply line 92 is made with finned tubing, with numerous fins 94 throughout its length. The expanded gas is exhausted through the outer lumen 84 over the helical gas supply line 92 and between the fins 94, pre-cooling and condensing the incoming fluid allowing the thermally transmissive region 64 to obtain lower temperatures.

The cryogenic systems are better understood with reference use in operative procedures. For example, as shown in FIG. 13 a catheter-based device can be used for an endocardial approach to tissue. Following the determination of a proposed lesion site within a heart chamber 96, the catheter 16 is directed through a blood vessel 98 to a region within the heart 100, such as an atrial or ventricular chamber, where the lesion will be made. The thermally-transmissive region 26 is placed proximate the nerve tissue to be ablated. The thermally-transmissive region of the catheter may be deformed to conform to the curvature of the nerve tissue before, during, or after placement against the tissue. The controller 18 allows or causes cryogenic fluid to flow from the cryogenic fluid supply 12 to the fluid path in the catheter 16 and thence to the thermally-transmissive region 26 to ablate the desired area or to cold map along the same target nerve area.

Figure 14:
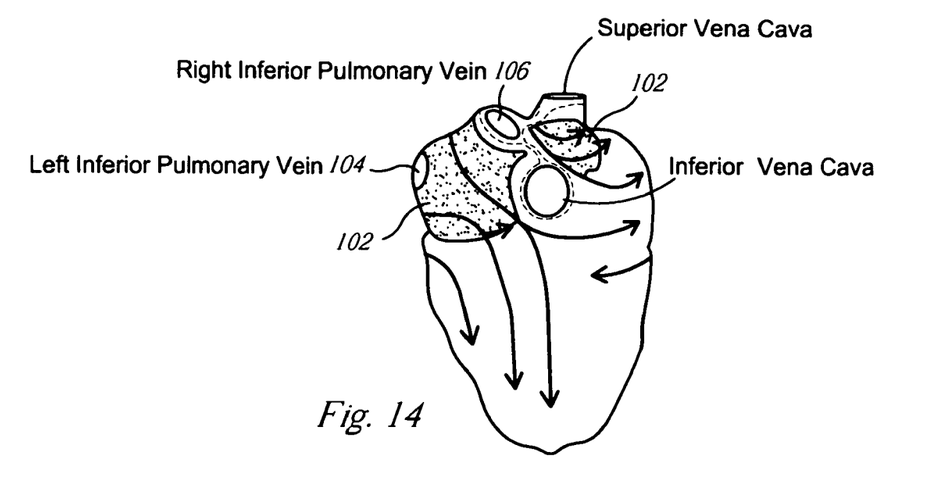
FIG. 14 is an illustration of the areas of the heart that receive treatment in accordance with the present invention.

Turning now to FIG. 14, a right posterior view of the heart is shown that illustrates possible treatment locations on the exterior surface of the heart for epicardial procedures performed with a rigid or semi-rigid probe, such as the device of FIG. 7. The shaded area 102 between the left inferior pulmonary vein (LIPV) 104 and the right inferior pulmonary vein (RIPV) 106 are treated by cooling or freezing tissue in order to modify the sympathetic nerve activity within the heart. This location is near the Ligament of Marshall (LOM), a vestigial fold of the pericardium located in the back of the left auricle, running from the coronary sinus upward to the left superior pulmonary vein. Another location of nerve tissue is between the superior vena cava and the inferior vena cava. The arrows shown in FIG. 14 represent nerve conduction pathways throughout the heart.

Figure 15:
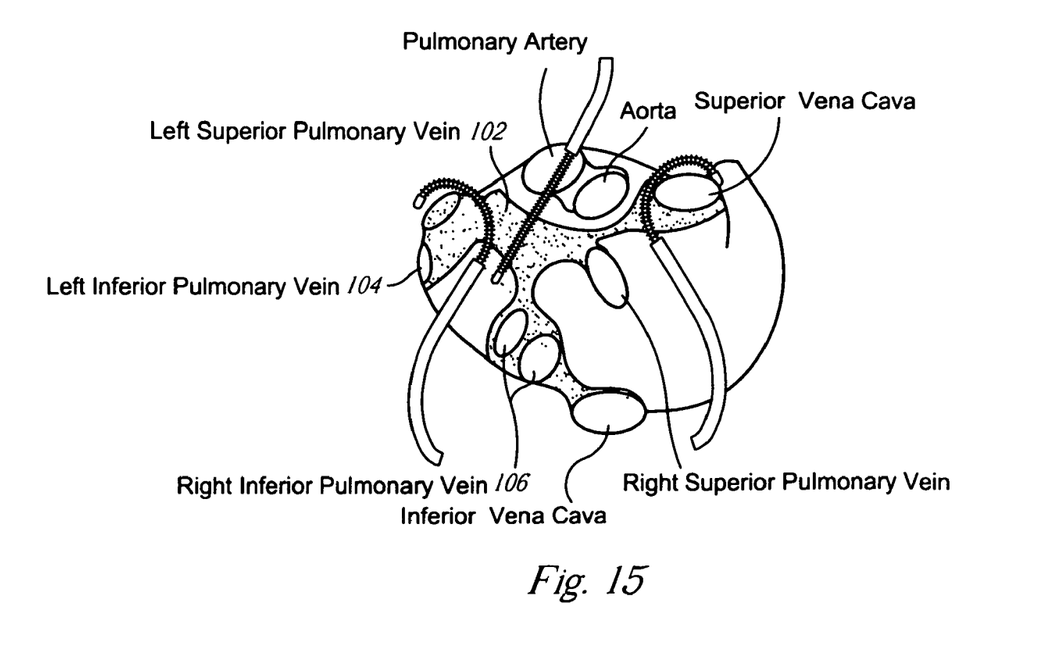
FIG. 15 is an alternative view showing the areas of the heart that receive treatment in accordance with the present invention including the location of the cooling device.

FIG. 15 illustrates a posterior top view of the heart. Once again, the shaded areas 102 represent target nerve locations that are to receive refrigerant from the ablation device. Several ablation devices are shown at various points on the surface of the heart where lesions might be made. For example, in an exemplary procedure, a probe is placed directly on the Ligament of Marshall and cooled to disable the nerves for a period of 20 to 30 days. To provide 30 days of pain relief following a thoracotomy, the probe and adjacent tissue are cooled to −80° C. for approximately 60 to 120 seconds.

Figure 16:
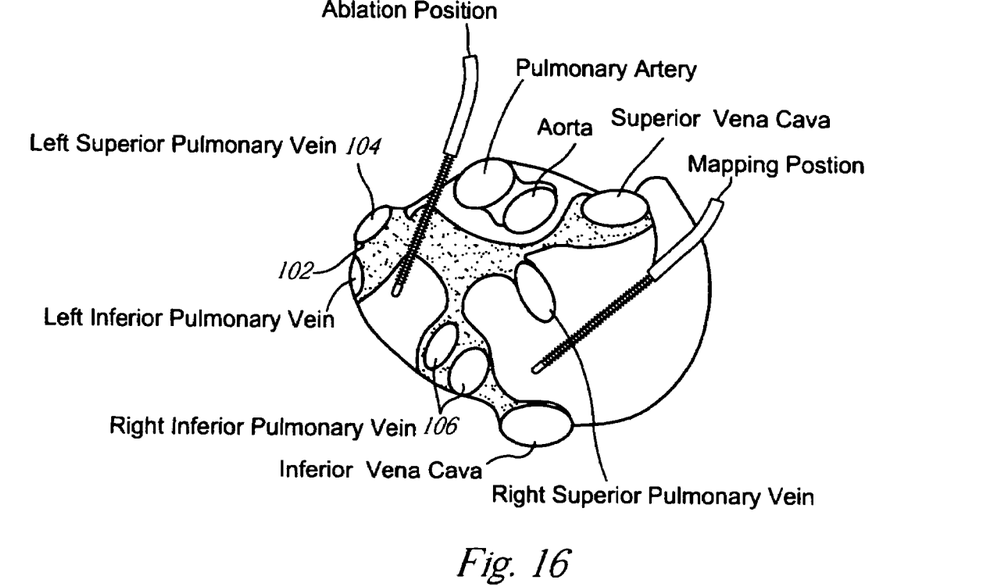
FIG. 16 is a perspective view of the areas of the heart that receive treatment in accordance with the present invention including the location of the cooling device for both mapping and ablation.

FIG. 16 once again shows the heart in a posterior top view. Shaded areas 104 represent nerve regions that may be cooled or cryoablated in order to effectively reduce the likelihood of atrial fibrillation. FIG. 16 also shows an ablation device that may be used to cold or ice map locations in the heart prior to cryoablation of the target nerve tissue. In some instances, the mapping may be done at one location, whereas the actual ablation may be performed at another location.

Figure 17:
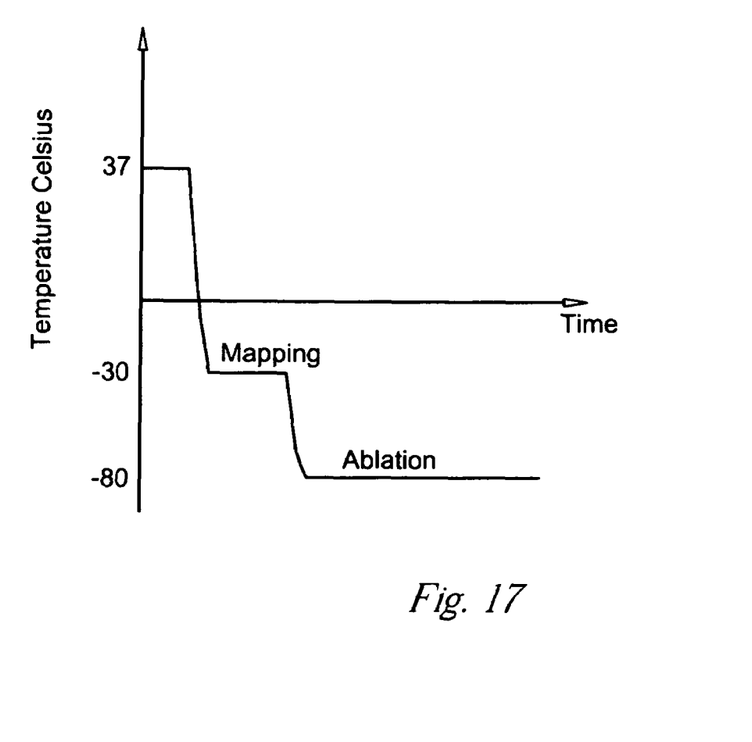
FIG. 17 is a graph illustrating the temperature ranges for mapping and ablation of the heart in accordance with the present invention.

FIG. 17 is a graphical representation of temperature vs. time. Mapping begins when the nerve tissue is cooled by the refrigerant delivered by the ablation device to a temperature of approximately 37 degrees Celsius. When the nerve tissue is cooled to a temperature of approximately −30 degrees Celsius, cryoablation occurs. However, cryoablation is more effective at a temperature of about −80 degrees Celsius.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of preventing postoperative transient arrhythmia, comprising the steps of:
    performing a surgical procedure on a heart; and
    postoperatively cooling selected cardiac nerves to a temperature below −30 degrees Celsius until nerve signal conduction in the selected cardiac nerves it at least temporarily inhibited.

2. The method of claim 1, wherein the selected cardiac nerves include nerves associated with a posterior surface of the left atrium of the heart.

3. The method of claim 1, wherein the selected cardiac nerves include sympathetic nerves proximate the Ligament of Marshall.

4. The method of claim 1, wherein the step of cooling has a duration of 15 to 120 seconds.

5. The method of claim 1, wherein the step of cooling is accomplished at a temperature of approximately −80 degrees Celsius.

6. The method of claim 1, wherein the selected cardiac nerves are approached endocardially.

7. The method of claim 1, wherein the selected cardiac nerves are approached epicardially.

8. The method of claim 1, wherein the selected cardiac nerves are stunned so that nerve signal conduction is temporarily inhibited.

9. The method of claim 1, wherein the selected cardiac nerves are ablated so that nerve signal conduction is permanently inhibited.

10. The method of claim 1, further comprising the step of cold mapping cardiac tissue prior to the step of cooling.

11. A method of preventing postoperative transient arrhythmia, comprising the steps of:
    performing a surgical procedure on a heart;
    epicardially approaching a selected region of the heart using a cooling device postoperatively;
    placing the cooling device on the surface portion of the heart; and
    using the cooling device to cool selected cardiac nerves to a temperature below −30 degrees Celsius.

* * * * *